United States Patent
Wooster et al.

(10) Patent No.: US 10,646,450 B2
(45) Date of Patent: May 12, 2020

(54) DELIVERY SYSTEM COMPRISING A CORE AND A DIGESTIBLE POLYMER SHELL

(71) Applicant: NESTEC S.A., Vevey (CH)

(72) Inventors: Timothy James Wooster, Epalinges (CH); Laurence Donato-Capel, Cheseaux sur Lausanne (CH); Anwesha Sarkar, Leeds Yorkshire (GB); Simone Acquistapace, La Tour-de-Peilz (CH)

(73) Assignee: Societe des Produits Nestle S.A., Vevey (CH)

(*) Notice: Subject to any disclaimer, the term of this patent is extended or adjusted under 35 U.S.C. 154(b) by 0 days.

(21) Appl. No.: 16/045,287

(22) Filed: Jul. 25, 2018

(65) Prior Publication Data
US 2018/0325827 A1 Nov. 15, 2018

Related U.S. Application Data

(62) Division of application No. 15/502,007, filed as application No. PCT/EP2015/067123 on Jul. 27, 2015, now Pat. No. 10,052,287.

(30) Foreign Application Priority Data

Aug. 7, 2014 (EP) ..................................... 14180139

(51) Int. Cl.
*A61K 9/28* (2006.01)
*A23L 5/00* (2016.01)
(Continued)

(52) U.S. Cl.
CPC .............. *A61K 9/2873* (2013.01); *A23L 5/00* (2016.08); *A23L 33/10* (2016.08); *A23P 10/30* (2016.08);
(Continued)

(58) Field of Classification Search
CPC .. A61K 9/2873; A61K 9/2806; A61K 9/2063; A23L 33/10; A23L 5/00; A23P 10/30; A23V 2002/00
See application file for complete search history.

(56) References Cited

U.S. PATENT DOCUMENTS

2004/0258803 A1  12/2004  Van Benthum et al.
2009/0004333 A1   1/2009  Nakhasi et al.
(Continued)

FOREIGN PATENT DOCUMENTS

CN  103301091  9/2013
JP  S6115733 A  1/1986
(Continued)

OTHER PUBLICATIONS

Gerez et al., "Whey Protein Coating Bead Improves the Survival of the Probiotic Lactobacillus Rhamnosus Crl 1505 to Low pH", Letters in Applied Microbiology, vol. 54, Issue No. 6, Mar. 2012, pp. 552-556, XP055162215.

(Continued)

*Primary Examiner* — Carlos A Azpuru
(74) *Attorney, Agent, or Firm* — K&L Gates LLP

(57) ABSTRACT

A delivery vehicle with a core surrounded by a digestible polymer shell having a melting and/or softening point above the body temperature of an animal or human, and where the core has a lipid and/or lipophilic active ingredient dispersed in a continuous polymer matrix. The delivery vehicle can be used to release lipid and/or lipophilic active ingredients, such as pharmaceuticals, nutraceuticals, supplements, traditional/herbal medicine, or combinations thereof, after a predetermined lag time following ingestion.

23 Claims, 6 Drawing Sheets

(51) Int. Cl.
   *A23P 10/30*   (2016.01)
   *A61K 9/20*    (2006.01)
   *A23L 33/10*   (2016.01)
   *A61K 31/20*   (2006.01)

(52) U.S. Cl.
   CPC .......... *A61K 9/2063* (2013.01); *A61K 9/2806* (2013.01); *A61K 31/20* (2013.01); *A23V 2002/00* (2013.01)

(56) References Cited

U.S. PATENT DOCUMENTS

| | | |
|---|---|---|
| 2011/0117180 A1 | 5/2011 | Yan et al. |
| 2011/0150995 A1 | 6/2011 | Josh |
| 2013/0034681 A1 | 2/2013 | Malessa et al. |

FOREIGN PATENT DOCUMENTS

| | | |
|---|---|---|
| JP | 2001342127 A | 12/2001 |
| JP | 2002531492 A | 9/2002 |
| JP | 2006506410 A | 2/2006 |
| JP | 2006510359 A | 3/2006 |
| JP | 2011254834 A | 12/2011 |
| JP | 2014054247 A | 3/2014 |
| WO | 2010004256 | 1/2010 |
| WO | 2013120856 A1 | 8/2013 |
| WO | 2014/078912 A1 * | 5/2014 |
| WO | 2014078912 | 5/2014 |

OTHER PUBLICATIONS

"Xanthan gum", Handbook of Pharmaceutical Excipients, 6th edition, 2009, pp. 782-785, XP055597900.

* cited by examiner

DELIVERY SYSTEM COMPRISING A CORE AND A DIGESTIBLE POLYMER SHELL

PRIORITY CLAIM

This application is a divisional of U.S. application Ser. No. 15/502,007 filed Feb. 6, 2017, which is a National Stage of International Application No. PCT/EP15/67123 filed Jul. 27, 2015, which claims priority to European Patent Application No. 14180139.9 filed Aug. 7, 2014, the entire contents of which are incorporated herein by reference.

FIELD OF THE INVENTION

The invention relates to a delivery vehicle and its use to release an active ingredient within the gastrointestinal tract (herein after the GI tract). More particularly the present invention relates to a delivery vehicle and its use to release an active ingredient within the GI tract after a pre-determined lag time following ingestion.

BACKGROUND

The benefits of delivery vehicles that can release an active ingredient after a pre-determined lag time following ingestion are well known to the nutrition, supplement and pharmaceutical industries. Such delivery vehicles can be used to ensure the release of an active ingredient at a particularly advantageous time following ingestion e.g. a time approximating to a particular stage of digestion and/or the metabolic cycle and/or a particular location within the GI tract e.g. the duodenum, ileum or colon. Additionally, such delivery vehicles can be used to ensure the release of an active ingredient at a particular time of the day or night e.g. a time in-keeping with biological rhythms and circadian variations.

Of particular interest to the aforementioned industries are delivery vehicles that can release a lipid and/or lipophilic active ingredient within the GI tract after a pre-determined lag time.

Lipid and/or lipophilic active ingredients are known to be advantageously employed in the treatment or management of a variety of conditions affecting the health of the GI tract e.g. ulcerative colitis, Crohn's disease, colorectal cancer, and/or GI tract infections, as well as in the treatment and management of obesity and other weight related conditions e.g. through the modulation of hunger, satiety and/or through the regulation of nutrient absorption.

A delivery vehicle that can release a lipid and/or lipophilic active ingredient within the GI tract after a pre-determined lag time can not only increase the amount of said lipid and/or lipophilic active ingredient reaching a particular location within the GI tract, it can also minimise, prevent or control the metabolic modification or metabolism of said ingredient e.g. because of digestion and/or first pass effects. Accordingly, said delivery vehicle can improve the bio availability and/or efficacy of said lipid and/or lipophilic active ingredient, and consequently reduce its minimum effective concentration.

Delivery vehicles that can release an active ingredient within the GI tract after a pre-determined lag time following ingestion are known. A widely used delivery vehicle for this purpose is one in which an active ingredient is encapsulated in a matrix material. In this type of delivery vehicle an active ingredient is usually dispersed throughout a continuous matrix material that dissolves as it progresses through the GI tract. Typically the encapsulated active ingredient is intermittently released over a period of time as the matrix material surrounding the dispersed active ingredient is dissolved. This intermittent/slow release can be a drawback of these delivery vehicles. This is especially true in the case of an active ingredient that has a narrow absorption window or, in relation to an active that is intended to treat a condition affecting a particular location within the GI tract e.g. Crohn's disease, ulcerative colitis, colorectal cancer, and/or GI tract infections. For these cases in particular, a delivery vehicle that not only releases an active ingredient within the GI tract after a predetermined lag time but, also does so in a continuous and preferably rapid manner is particularly desirable.

Delivery vehicles that can release an active ingredient in a continuous and rapid manner are also known. The most widely used of these are delivery vehicles having an enteric coating. Enteric coatings form protective barriers around an active ingredient. However, enteric coatings have known drawbacks, for example the dissolution of enteric coatings at high pH and under conditions wherein there is a high water activity (AO, can make their application to emulsion based systems difficult e.g. those comprising lipid and/or lipophilic active ingredients. Furthermore, the dissolution of enteric coatings at higher pH values means that delivery of active ingredients within the GI tract is often restricted to the initial part of the small intestine Viz. the duodenum.

Accordingly, there remains a need for a delivery vehicle that avoids or mitigates one or more of the drawbacks and problems highlighted above.

SUMMARY

According to the invention there is provided a delivery vehicle comprising a core (1) surrounded by a digestible polymer shell (4) having a melting and/or softening point above the body temperature of an animal or human, wherein said core comprises a lipid and/or lipophilic active ingredient (2) dispersed in a continuous polymer matrix (3).

The invention is set out in the claims. Because the time taken, following ingestion, for the digestible polymer shell (4) to be compromised e.g. by dissolution, erosion, digestion and/or degradation, can be tailored by varying its chemical and/or physical properties, the lag time following ingestion, before the release of the lipid and/or lipophilic active ingredient (2) can be pre-determined.

The pre-determined lag time can be approximated to a particular stage of digestion and/or the metabolic cycle and/or a particular location within the GI tract e.g. the duodenum, ileum or colon.

This enables the delivery vehicle of the invention to be used to release lipid and/or lipophilic active ingredients, such as pharmaceuticals, nutraceuticals, traditional/herbal medicines, supplements or combinations thereof, within or at a particular location of the GI tract e.g. the ileum or colon, and/or at a particular time after ingestion so as to minimise, prevent or control the metabolic modification or metabolism of said ingredient e.g. because of digestion and/or first pass effects.

Accordingly, a delivery vehicle of the invention may be advantageously employed to deliver lipid and/or lipophilic active ingredients for the prevention and/or treatment of diseased states e.g. ulcerative colitis, Crohn's disease, infections of the GI tract, colorectal cancer and combinations thereof, and/or cosmetic issues such as excess weight and aging.

If the continuous polymer matrix (3), which is preferably a biopolymer matrix, is a solid e.g. a gel below body temperature, and solid or liquid at body temperature or above, a continuous, and preferably rapid, release of the lipid and/or lipophilic ingredient (2), following the pre-determined lag time, can be achieved.

Optionally the lipid and/or lipophilic active ingredient (2) present within the core may be dispersed as a fine emulsion using an emulsifier. The more finely dispersed the lipid and or lipophilic active ingredient, the higher the rate of digestion/absorption may be when said lipid and/or lipophilic active is released in the GI tract.

Optionally the core (1) of the delivery vehicle comprises a weighting agent and/or the digestible polymer shell (4) comprises a thickener. These can help to ensure the evenness of the digestible polymer shell (4) surrounding the core (1), and can thereby can help ensure the reproducibility of the pre-determined lag time following ingestion.

DRAWINGS

Embodiments of the invention will now be described, by way of example, with reference to the following drawings.

Figure 4:
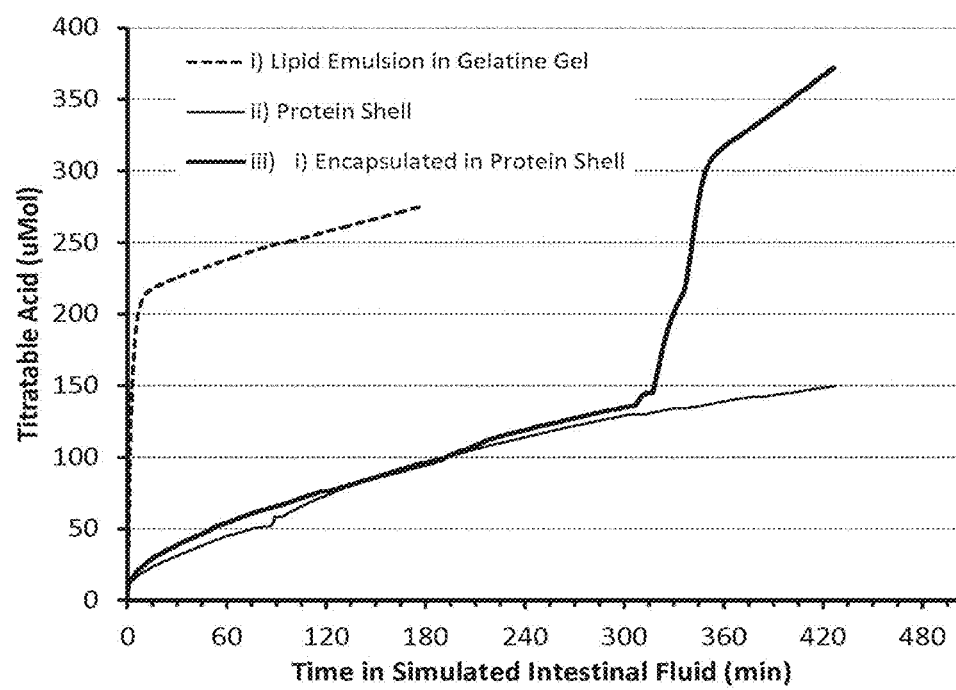

FIG. 4 shows a comparison, in simulated intestinal fluid at 25° C., of i) of the lipid digestion/release profile a lipid (coriander oil) trapped within a gelatine polymeric matrix (gel), ii) the digestion profile of a cross-linked β-lactoglobulin/xanthan digestible polymer (gel), iii) the lipid (coriander oil) digestion/release profile of a lipid (coriander oil) from a delivery vehicle of the invention as described in example 2 (gelatine, β-lactoglobulin/xanthan delivery system).

Figure 5:
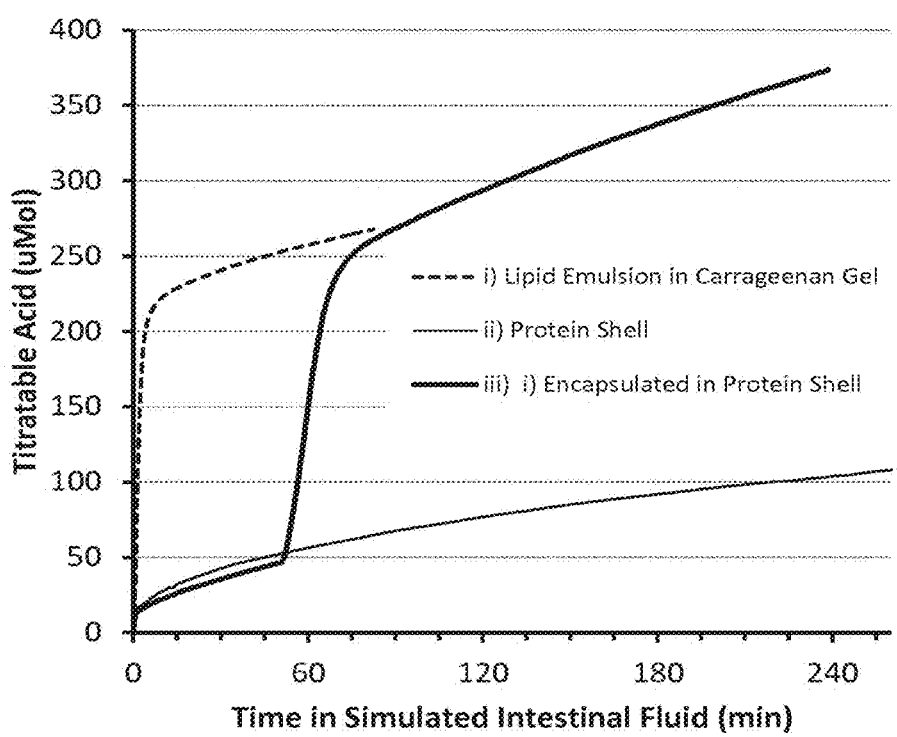

FIG. 5 shows a comparison of the lipid digestion/release profile, in simulated intestinal fluid at 25° C., of i) a lipid (DHA/EPA tuna oil) emulsion trapped within a carrageenan polymeric matrix (gel), ii) the digestion profile of a cross-linked β-lactoglobulin/xanthan digestible polymer (gel), iii) the lipid (coriander oil) digestion/release profile of a lipid (DHA/EPA tuna oil) in a delivery vehicle of the invention as described in example 4 (carrageenan, β-lactoglobulin/xanthan delivery system).

Figure 6:
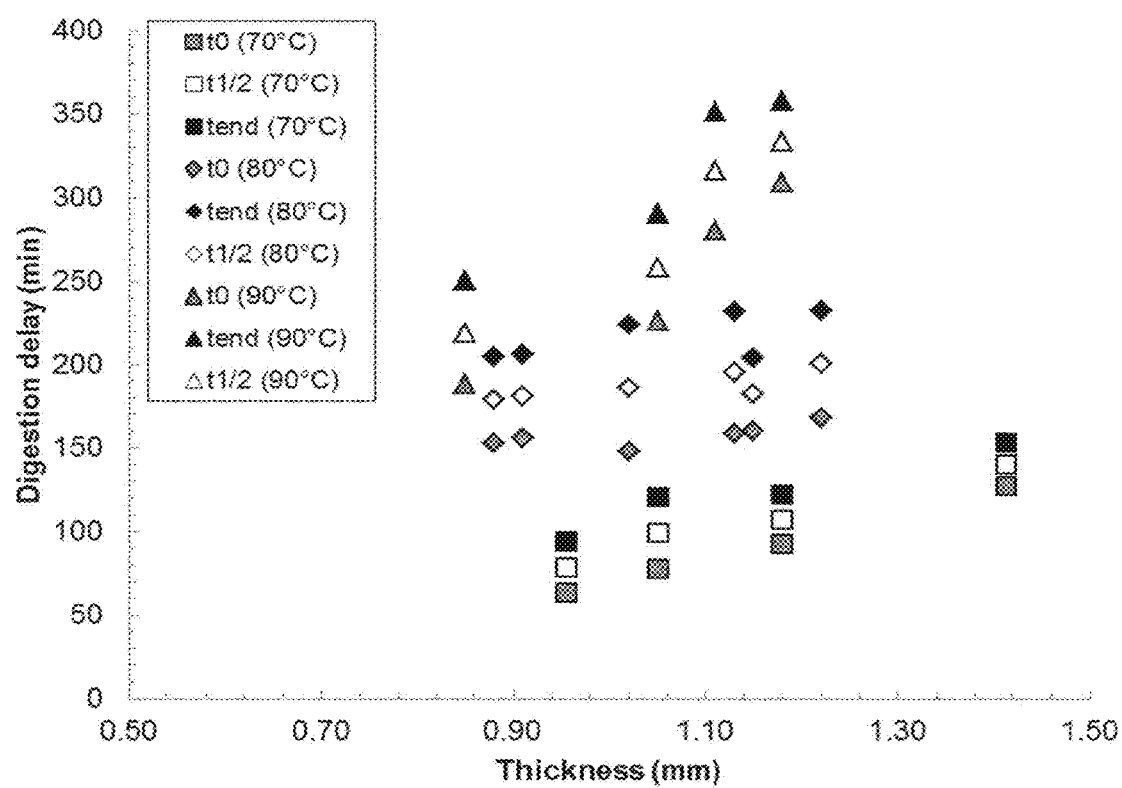

FIG. 6 shows the digestion delay or lag time ($T_o$) before the release of an encapsulated lipid (coriander oil), the time when at least 50% of an encapsulated lipid (coriander oil) is released ($T_{1/2}$) and the time when all of an encapsulated lipid (coriander oil) is released ($T_{end}$), from β-lactoglobulin/xanthan delivery vehicles of the invention manufactured as set out in example 2 having different digestible polymer shell (4) thicknesses which have been cross-linked at 70° C., 80° C. or 90° C.

DETAILED DESCRIPTION

In a first aspect of the invention there is provided a delivery vehicle comprising a core (1) surrounded by a digestible polymer shell (4) having a melting point and/or softening point above the body temperature of an animal or human, wherein said core comprises a lipid and/or lipophilic active ingredient (2) dispersed in a continuous polymer matrix (3).

Surprisingly the inventors have found that a delivery vehicle in accordance with the invention can release the lipid and/or lipophilic active ingredient (2) comprised within the core (1) after a pre-determinable lag time following ingestion by a subject e.g. via oral consumption or nasogastric and other enteral feeding methods. Advantageously this pre-determinable lag time following ingestion can be equated or approximated to a particular stage of digestion and/or the metabolic cycle; to a particular location within the GI tract e.g. the duodenum, ileum or colon; and/or to a particular time of the day or night depending upon when the delivery vehicle was ingested e.g. a time in-keeping with biological rhythms and circadian variations.

The term "softening point" as used herein refers to the temperature at which a material e.g. a polymer, loses its solid characteristics and becomes relatively fluid. A material's softening point can be measured using the standard ball and ring method from the American Society of Testing Materials. Alternatively, a materials softening point can be determined from measurements of its viscoelasticity, using either rheological measurements (as per Paar Physica test methods) or dynamic thermal mechanical analysis measurements (as per American Society of testing methods), wherein the softening point is defined as the point at which the storage modulus is lower than the loss modulus.

The term "lag time" as used herein refers to the length of time following ingestion before the digestible polymer shell (4) is compromised e.g. via digestion, degradation and/or dissolution, and the lipid and or lipophilic active ingredient (2) is released within the GI tract of a subject.

The term "subject" as used herein refers to any type of animal, more particularly any type of mammal, and most particularly a cat, a dog or a human.

The term "polymer matrix" as used herein refers to a three-dimensional network formed from a polymer or polymers, including cross-linked polymer or polymers. The three-dimensional network may be formed by the interaction e.g. chemical and/or physical of a polymer or polymers units/chains.

The polymer matrix (3) may be an aqueous polymer matrix e.g. an aqueous gel.

In an embodiment of the invention the polymer matrix (3) is solid below the body temperature of an animal and/or human, and solid or liquid at or above the body temperature of an animal and/or human.

Normal body temperature of an animal or human is 35° C.-40° C., 36° C.-38° C., 36° C.-37.5° C.

If the polymer matrix (3) is solid e.g. a gel, below body temperature then this enables the core (1) of the delivery vehicle, comprising the dispersed lipid or lipophilic active (2), to be kept in a solid state during manufacturing and/or storage. This can prevent the dispersed lipid or lipophilic active (2) and/or polymer matrix (3) from leaking into and being dispersed throughout the digestible polymer shell (4) during manufacturing or storage. It also enables said core (1) to be centred and uniformly surrounded by the digestible polymer Shell (4).

These attributes can help to ensure the reproducibility of the pre-determined lag time.

If the polymer matrix (3) is a liquid at body temperature or above, then upon ingestion by an animal or human, the core (1) of the delivery vehicle will be a liquid. This has the advantage that after expiry of the lag time, all of the lipid and/or lipophilic active ingredient (2) comprised within the core (1), or substantially all, will be released continuously, and preferably rapidly. This is particularly relevant when the polymer matrix (3) is a dense or tortuous polymeric matrix having an average mesh/pore size of 50 nm.

This is also particularly advantageous if the lipid or lipophilic active ingredient (2) has an absorption window and/or, in the case wherein the lipid and/or lipophilic active ingredient (2) is intended to treat a particular location within the GI tract, and/or wherein it is desirable to release the lipid and/or lipophilic active ingredient (2) at a pre-determined time after ingestion equating to a particular stage of digestion and/or the metabolic cycle e.g. to minimise/avoid liver metabolism of said active ingredient.

The term "absorption window" as used herein refers to a particular location (an area or region) in the GI tract wherein an active ingredient is absorbed more efficiently or at a higher rate in comparison to other locations within the GI tract.

It is preferred that all, or substantially all, of the lipid and/or lipophilic active ingredient (2) comprised within the core (1) is released within 75 minutes, 45 minutes, 30 minutes, 20 minutes, 15 minutes, 13 minutes, 10 minutes or 5 minutes, after expiry of the lag time.

By substantially all is meant up to 50%, 60%, 70%, 80%, or 90% of the lipid and or lipophilic active ingredient comprised therein. It is particularly preferred if 50% or more of the lipid and/or lipophilic active is released within 45 minutes after expiry of the lag time, and/or 80% of the lipid and/or lipophilic active is released within 75 minutes after the expiry of the lag time.

The polymer matrix (3) can be formed from any synthetic polymer, biopolymer, or combination thereof capable of interacting e.g. chemically or physically, and forming a polymer matrix e.g. by hydrogen bonding and/or by inter-winding of the polymer units and/or by crosslinking i.e. through ionic or covalent bonding. In particular the polymer matrix (3) may be formed from one or more cross-linked polymers.

Methods of performing crosslinking are well known in the art and it is well within the purview of the skilled person to select a particular crosslinking method.

Non limiting examples of cross linking methods include:

Covalent bindings such as for example induced by disulphides bonds related to cysteine chemistry, enzymatic treatment such as for example transglutaminase; non covalent bindings such as hydrogen, hydrophobic, ionic bindings; or bindings induced by addition of salts such as tripolyphosphate, or chemical such as gluteraldehyde, genipin.

Bindings may be induced by physical or chemical treatments including temperature (thermal cross-linking), pressure treatment, enzymatic treatment and/or addition of salts.

The term "Biopolymer" as used herein refers to any naturally occurring or modified food, pharmaceutical or agricultural grade polysaccharide, protein, polypeptide, polynucleotide or combinations thereof.

Non-limiting examples of biopolymers include: milk proteins e.g. caseins, micellar caseins, caseinates, whey proteins, β-lactoglobulin, α-lactalbumin, bovine serum albumin, lactoferrin, plant proteins e.g. potato proteins, patatin, protease inhibitors, soy protein, canola protein, pea protein, animal protein e.g. collagen, gelatin, egg protein e.g. ovalbumin, lysozyme; polysaccharides e.g. xanthan, pectin, cellulose, gellan, fibronectin, laminin, carrageenan, agar, gelatine, guar gum, locust bean gum, hyaluronic acid, water soluble salts of alginic acid such as sodium alginate, gum karaya, gum tragacanth, carrageenans, konjac mannan, and combinations thereof.

In a particular embodiment the polymer matrix (3) is formed from one or more biopolymer. More particularly the polymer matrix (3) is formed from one or more biopolymer selected from the group consisting of: gelatine, carrageenans, pectin, alginates, agar, gellan, konjac mannan, guar gum, gellan gum, locust bean gum and combinations thereof.

The core (1) of the delivery vehicle may comprise up to 30%, 0.25 to 15 wt %, 1-10 wt %, or 0.25 to 5 wt % of the polymer or polymers used to form the polymer matrix (3).

The lipid and/or lipophilic active ingredient (2) dispersed within the polymer matrix (3) can be any lipid or lipophilic compound that produces a desired result upon administration to a subject. Non limiting examples of lipid or lipophilic active ingredients include; pharmaceuticals, nutraceuticals, supplements, or any combination of the foregoing.

The term "lipid" as used herein refers to any compound that is insoluble in water but is soluble in non-polar organic solvents. Non limiting examples include fats, oils, waxes, sterols The term "lipophilic" as used herein refers to any compound that combines with or is soluble in lipids.

Non limiting examples of lipid and lipophilic active ingredients include; phospholipids, triglycerides, diglycerides, monoglycerides, ceramides, glycolipids and sphingolipids, carotenoids, phytosterols, phytosterol esters, polyphenols, cholesterol, cholesterol esters, fatty acids and esters thereof e.g. butyric acid, butyric acid, petroselinic acid, and eicosapentaenoic acid, diterpenoids and esters thereof e.g. retinol and retinol esters and, fish oil.

In a particular embodiment the lipid or lipophilic active ingredient is selected from the group consisting of: phospholipids, triglycerides, carotenoids, phytosterols, fatty acids and esters thereof e.g. petroselinic acid, eicosapentaenoic acid, butyric acid, and combinations thereof.

The total concentration of any lipid and/or lipophilic active ingredients dispersed within the polymeric matrix (3) of the delivery vehicle can be up to 80 wt %, up to 60 wt %, up to 40 wt %, up to 20 wt %, up to 10 wt % of the core (1) of the delivery vehicle.

The concentration of the lipid and/or lipophilic active ingredients (2) dispersed in the polymeric matrix (3) will depend on the characteristics of said active ingredient(s) to be employed e.g. its effective concentration, on its purpose e.g. the condition to be treated/prevented, as well as on the subject to be treated.

It is well within the purview of the skilled person to decide upon an appropriate concentration for a particular lipid and/or lipophilic active ingredient or combination thereof.

Typically, the concentration will depend on the type, age, size and health status of the subject, on the subject's lifestyle, as well as on its genetic heritage.

The core (1) of the delivery vehicle of the invention may comprise an emulsifier An emulsifier can stabilise the dispersed lipid or lipophilic active ingredients (2) against coalescence and can prevent or minimise flocculation. An emulsifier can also help to more finely disperse the lipid and/or lipophilic active ingredient (2) within the polymeric matrix (3). The more finely dispersed the lipid and or lipophilic active ingredient, the higher the rate of digestion/absorption may be when said lipid and/or lipophilic active is released in the GI tract.

The emulsifier may be any type of surfactant suitable for ingestion by a subject. In particular the emulsifier may be selected from the group consisting of: synthetic surfactants, natural surfactants, ionic surfactants, non-ionic surfactants, lecithins, proteins, surface active polysaccharides and combinations thereof. More particularly the emulsifier may be a protein, e.g. gelatine, myoglobin, myosin, preferably a dairy protein, a whey protein isolate, β-lactoglobulin, α-lactalbumin, bovine serum albumin, lactoferrin, casein, gum Arabic/ acacia, sugar beet pectin, polysorbates, polyglycerol esters of fatty acids, sucrose esters of fatty acids, citric acid esters of fatty acids, lecithins, lysolecithins, galactolipids, mono or diglycerides, sapoins, or combinations of any of the foregoing.

The concentration of the emulsifier may be up to 10 wt %, particularly 0.01 wt % to 5 wt %, particularly 0.1 to 3 wt % of the core (1) of the delivery vehicle.

The core (1) of the delivery vehicle of the Invention may comprise a weighting agent.

The core (1) of the delivery vehicle can contain a significant amount of the lipid and/or lipophilic active ingredient (2), because of this the core (1) can to float in denser mediums. This can make centering the core (1) and uniformly surrounding it by the digestible polymer Shell (4) difficult. A weighting agent can minimize this phenomenon by increasing the density of the core (1). This can help ensure the reproducibility of the pre-determined lag time.

Non limiting examples of weighting agents include; brominated vegetable oil, SAIB/sucrose diacetate hexaisobutzrate, ester gums such as glycerol esters of wood rosin, elemi gum, damar gum, and combinations thereof.

The amount of weighting agent comprised in the core can be up to 50 wt %, up to 40 wt %, up to 30 wt %, up to 10 wt %, up to 5 wt % of the core (1) of the delivery vehicle.

The core (1) may also comprise a disintegrating agent or a mixture of disintegrating agents commonly used in delivery vehicles e.g. tablets, capsuled and microcapsules, wherein a continuous and/or rapid release is desired. Such ingredients are well known to the person skilled in the art. Non limiting examples of the type of disintegrating agents that may be useful include agents that effervesce and or swell in the presence gastric juices and thereby provide a force that can help to further compromise or disrupt the digestible polymer shell (4).

The core may also contain any other excipients commonly used in delivery vehicles e.g. Capsules, microcapsules and tablets. Examples of compounds commonly used in delivery vehicles can be found in, for example, Pharmaceutical Dosage Forms—Tablets Rational Design and Formulation, L. L. Augsburger (Ed), S. W. Hoag (Ed), Informa, 2008, ISBN: 9780849390159.

The core (1) of the delivery vehicle is surrounded by a digestible polymer shell (4) having a melting point and/or softening point above the body temperature of an animal or human (hereinafter the digestible polymer shell). As the delivery vehicle progresses through the GI tract, the digestible polymer shell (4) serves to protect the core (1) of the delivery vehicle, and thus the lipid and/or lipophilic active ingredient (2) comprised within the polymer matrix (3), until the expiry of the pre-determined lag time.

The term "digestible polymer" as used herein refers to a cross-linked polymer or cross-linked mixture of polymers that is soluble, degradable and/or able to be digested, or partially digested, within the stomach, the small intestine and/or the colon of a subject.

Methods of performing crosslinking are well known in the art. Non limiting examples are listed herein above. It is well within the purview of the skilled person to select a particular crosslinking method. In particular the digestible polymer may be thermally crosslinked. This has the advantage that the crosslinking involves covalent bonds and can make the integrity of the digestible polymer shell (4) less sensitive to changes in pH and temperature. More particularly the digestible polymer may be cross-linked using thermally ted cysteine cross linking. This has the advantage that the degree of crosslinking can be tailored by selecting/designing, proteins with different numbers of cysteine residues and/or by controlling the degree of thermal exposure (time×temperature).

In a particular embodiment the digestible polymer comprised within the digestible polymer shell (4) may be one or more biopolymer, more particularly one or more thermally crosslinked biopolymer or one or more biopolymer cross-linked using thermally activated cysteine cross linking.

Biopolymers have the advantage that their inclusion in human and animal products for ingestion e.g. food products is more acceptable. Even more particularly, the digestible polymer comprised within the digestible polymer shell (4) may be one or more protein biopolymer.

Non limiting examples of protein biopolymers include: milk proteins e.g. caseins, micellar caseins, caseinates, whey proteins, β-lactoglobulin, α-lactalbumin, bovine serum albumin, lactoferrin, plant proteins e.g. potato proteins, patatin, protease inhibitors, soy protein, canola protein, pea protein, animal protein e.g. collagen, gelatin, egg protein e.g. ovalbumin, lysozyme, milk proteins myofibrilar proteins, pea proteins, lupin, rice protein, gluten, lysozyme and/or myosin, and combinations thereof.

More particularly the digestible polymer comprised within the digestible polymer shell (4) is selected from the group consisting of: Bovine serum albumin, β-lactoglobulin lactoferrin, patatin, soy protein, canola protein, pea protein, egg protein e.g. ovalbumin, lysozyme, pea proteins, lupin, rice protein, gluten, lysozyme, zein, and a combination thereof.

In an embodiment the one or more protein biopolymer is cross linked e.g. by cysteine chemistry. This process is induced by temperature treatment, pressure treatment, addition of cysteine containing chemical or incubation at chilled temperatures for extended periods of time, in particular the one or more protein biopolymer is cross-linked using thermally activated cysteine cross linking. The digestible polymer shell (4) may comprise up to 100 wt %, 2 wt %-50 wt %, 1 wt %-20 wt %, 1-10 wt % of the digestible polymer.

The lag time may be tailored by varying the chemical and/or physical properties of the digestible polymer shell (4).

Non limiting examples of chemical and physical properties that may be varied include: composition, thickness, microstructure, porosity, density, tortuousness.

The thickness of the digestible polymer shell (4) of the delivery vehicle of the invention may range from 0.001 to 10 mm. However, more particularly the thickness of the digestible polymer shell (4) will be within a range from 0.001 mm to 10 mm, 0.001 mm to 5 mm, 0.005 mm to 3 mm, 3 mm to 10 mm, or 3 mm to 5 mm.

The thickness will depend upon chemical and/or physical properties of the digestible polymer shell (4) e.g. the particular digestible polymer and, on the desired pre-determined lag time.

The digestible polymer comprised within the digestible polymer shell (4) may form a dense/tortuous polymer matrix.

The term "polymer matrix" is defined hereinabove.

A benefit of the digestible polymer, comprised within the digestible polymer shell (4), forming a dense/tortuous polymer matrix is that it can make the digestible polymer shell (4) more resistant to dissolution, digestion and/or degradation in the GI tract. Digestive enzymes or the like, must first work their way through and/or erode the dense/tortuous polymer network before the digestible polymer shell (4) is compromised e.g. is digested/disrupted and, the lipid and/or lipophilic active ingredient (2) dispersed in the polymer matrix (3) of the core (1) is released.

By altering the tortuousness of the digestible polymer or polymers comprised within the digestible polymer shell (4), the diffusion of for example digestive enzymes through the digestible polymer matrix may be varied e.g. slowed. This may be because the digestible polymer mesh/pore size is modified e.g. narrowed so that the mesh/pores do not allow, or hinder, diffusion e.g. of digestive enzymes, through the digestible polymer matrix, and/or because the digestible polymer matrix interacts with for example the digestive enzymes via electrostatic, ionic or hydrophobic interactions, and/or because the diffusion path of for example digestive enzymes is long because of the many tight and twisting channels comprised within the digestible polymer matrix.

One measure that can be used to determine whether a digestible polymer or polymers forms a dense or tortuous polymer matrix is average mesh/pore size.

Mesh/pore size can be measured via probe diffusion measurements using techniques such as nuclear magnetic resonance, for example as outlined in Chui, M. M.; Phillips, R. J.; McCarthy, M. J., Measurement of the Porous Microstructure of Hydrogels by Nuclear Magnetic Resonance. *Journal of Colloid and Interface Science* 1995, 174, 336-344; particle tracking, for example as outlined in Fatin-Rouge, N.; Starchev, K.; Buffle, J., Size Effects on Diffusion Processes within Agarose Gels. *Biophysical Journal* 2004, 86, 2710-2719; and/or Fickian diffusion measurements, for example as outlined in Klak, M. C.; Picard, J.; Giraudier, S.; Larreta-Garde, V., Mastered proteolysis of gelatin gel can control the delivery kinetics of entrapped large molecules. *Soft Matter* 2012, 8, 4750-4755.

In the context of the invention, a digestible polymer is considered to form a dense/tortuous polymer matrix if the digestible polymer shell it forms has an average mesh/pore size of <50 nm, <45 nm<25 nm, <15 nm.

As will be immediately apparent to the skilled person, a wide variety of lag times can be obtained depending on the chemical and/or physical properties of the digestible polymer shell e.g. tortuousness, thickness, shape and composition. It is well within the purview of the skilled person to vary said properties and thereby arrive at a desirable pre-determined lag time.

Depending upon the chemical and physical properties of the digestible polymer shell the lag time may be up to 8 hours, up to 5 hrs, up to 3 hrs, or 0.5 hr to 3 hrs.

Lag time, and the time for release of a percentage of the lipid and/or lipophilic active comprised within the delivery vehicle of the invention, may be pre-determined in-vitro using methods and apparatus well known in the art. The United States Pharmacopedia (USP) describes several such methods e.g. dissolution tests 1-4 using USP simulated gastric and/or simulated intestinal media as outlined in USP 29.

Alternatively lag time, and the time for release of a percentage of the lipid and/or lipophilic active comprised within the delivery vehicle of the invention, may be predetermined using devices such as the TNO intestinal model—TIM1 model, the dynamic model gut, or other in vitro tests (e.g. pH-STAT titrator) as outlined in Beisson, F.; Tiss, A.; Riviere, C.; Verger, R., Methods for lipase detection and assay: a critical review. *Eur. J. Lipid Sci. Technol.* 2000, 102, 133-153 or, Golding, M.; Wooster, T. J., The influence of emulsion structure and stability on lipid digestion. *Current Opinion in Colloid and Interface Science* 2010, 15, 90-101.

Alternatively lag time, and the time for release of a percentage of the lipid and/or lipophilic active comprised within the delivery vehicle of the invention, may be determined via clinical assessment of digestion and absorption of the digestible polymer shell (4) and lipid and/or lipophilic active ingredient such as described in; Keogh, J. B. Wooster, T. J. Golding, M. Day. L. Otto, B. Clifton, P. M. Slowly and rapidly digested fat emulsions are equally satiating but their triglycerides are differentially absorbed and metabolized in humans., *J. Nutrition,* 2011, 141(5), 809-815.

The digestible polymer shell (4) of the delivery vehicle can also contain a thickener.

As stated hereinabove, the core (1) of the delivery vehicle can contain a significant amount of the lipid and/or lipophilic active ingredient (2) and because of this the core (1) can to float in denser mediums. This can make centering the core (1) and uniformly surrounding it by the digestible polymer shell (4) difficult. A thickener can minimize this phenomenon by increasing the viscosity of the digestible polymer shell (4). This can help ensure the reproducibility of the pre-determined lag time.

In a particular embodiment the digestible polymer shell (4) comprises a thickener.

Non limiting examples of thickeners include: xanthans, carrageenans, Konjac, Sugar beet pulp, Sunflower pulp, Mango pulp, Potato, Citrus PFP4, arabic gum, Karaya gum, colosan, tomato powder, Nèrè oligels, Bluten, pea protein, lupin flour, Dextran, chitosan, acacia gum, galactomannans, alginates guar gum, pectins, celluloses, starch, modified starch, citrus fibre, aggregated/microparticulated proteins, and combinations thereof.

In a particular embodiment, the thickener is selected from the group consisting of: Xanthans, carrageenans, guar gum, and combinations thereof.

The amount of thickener comprised in the shell can be up to 1.5 wt %, particularly up to 1 wt %, particularly 0.1-1 wt %.

The digestible polymer shell (4) of the delivery vehicle may be coated with one or more coatings.

Non limiting examples of suitable coatings include taste masking coatings, enteric coatings, coatings that impart a surface colour or surface finish.

The coating may also contain other common excipients such as lubricants, colourants, binders, diluents, glidents.

In order to achieve the continuous and preferably rapid release of the lipid and/or lipophilic active (2) after the lag time following ingestion, it is preferable that the digestible polymer shell (4) or any coating thereon, contains no, or substantially no, ingredients that are diffusion barriers or swell to such an extent that they act as a diffusion barrier to the release of said lipid and/or lipophilic active (2). The lipid and/or lipophilic active (2) should be released from the delivery vehicle of the invention as a result of the physical rupturing and/or disintegration and/or digestion of the digestible polymer shell, and not as a result of the diffusion of said lipid and/or lipophilic active (2) through said digestible polymer shell (4) or any coating thereon.

Non limiting examples of diffusion barriers include; Lipids, wax coatings such as cocoa butter, canuba wax, and hydrocolloid coatings such as ethylcellulose.

Non limiting examples of swelling agents that can swell to such an extent that they act as a diffusion barrier are hydrophilic cross-linked polymers, which swell from 10 to 1,000 times their own weight when placed in an aqueous medium e.g. polymethacrylate co-polymers, croscarmellose sodium, crospovidone, low-substituted hydroxypropyl cellulose, sodium starch glycolate (Explotab), Citrus fibres, Starch.

Water soluble and/or amphiphilic or amphipathic active ingredients and/or class II poorly soluble drugs may also be included in the delivery vehicle disclosed herein. Said active ingredients may, for example, be comprised within the polymer matrix (3) and/or, comprised within the core (1) and/or, comprised within the digestible polymer shell (4).

The term "hydrophilic" refers to any compound that is attracted to water or polar substances.

The term "amphiphilic or amphipathic" refers to any compound that may be solubilised within interfacial, colloidal or micellar structures.

The water soluble and/or amphiphilic or amphipathic active ingredients can be any type of compound. In particular said active ingredients can be pharmaceuticals, nutraceuticals, supplements, Vitamins or combinations of the foregoing.

The delivery vehicle of the invention may be any shape, but would normally be a shape selected from the group consisting of: spherical, elongated, ellipsoidal, oblate ellipsoidal, or cylindrical.

The delivery vehicle disclosed herein can be prepared by methods well known in the art. Different methods may be selected depending on the desired dimensions of the delivery vehicle.

The delivery vehicle disclosed herein may be prepared by a process comprising:
Adding a lipid and/or lipophilic active ingredient (2), optionally with a weighting agent and/or an emulsifier, to a solution and mixing,
Homogenising the above formed mixture,
Adding the polymer matrix (3) polymer to said mixture,
Heating the above mixture until the polymer matrix polymer melts and the mixture becomes homogeneous,
Optionally crosslinking the polymer matrix (3) polymer, for example by heating, adjusting the pH e.g. to 6.5-8 and ionic strength of the above formed mixture to the desired value through the addition of an acid and/or base (HCl and/or NaOH) and salts such as NaCl or $CaCl_2$,
Forming a shape from said mixture using for example moulding, templating or injection techniques or, forming the mixture into small droplets using emulsion templating, 3 d printing, micro or milli fluidics, or jet extrusion,
Placing said formed shapes or, small droplets, in a solution of the digestible polymer of the digestible polymer shell (4), optionally with a thickener,
Forming a shape from said mixture and crosslinking the digestible polymer of the digestible polymer shell (4) for example by heating, adjusting the pH e.g. to 6.5-8 and/or ionic strength of the above formed mixture to the desired value through the addition of an acid and/or base (e.g. HCl and/or NaOH) and monovalent (e.g. NaCl), divalent (e.g. CaCl2) or polyvalent (e.g. Fe(III) $Cl_3$) salts.

Further details of suitable preparation processes are set forth in the examples included herein.

The delivery vehicle of the invention may be a consumable product in its own right, or it may be added to a consumable product.

In an embodiment of the invention there is provided a consumable product comprising a delivery vehicle as defined herein.

The term "consumable product" as used herein refers to any product that can be placed in the mouth and ingested and/or fed to a subject e.g. via nasogastric and other enteral feeding methods.

The delayed delivery systems of the invention may be added to a consumable product by ways well known in the art e.g. by direct mixing.

Non limiting examples of consumable products which may comprise the delivery vehicles of the invention include; pharmaceutical products, nutraceuticals products, medical foods, traditional/herbal medicines, veterinary products including pet food and pet care products and, foodstuffs of any kind including functional foods and food supplements.

As stated herein, a delivery vehicle of the invention may be used to release a lipid and/or lipophilic active ingredient (2) within the GI tract after a pre-determined lag time, following ingestion.

Because the predetermined lag time can be approximated to a particular stage of digestion and/or the metabolic cycle and/or a particular location within the GI tract e.g. the duodenum, ileum or colon; and because the predetermined lag time may also be equated to a particular time of the day or night depending upon when the delivery vehicle was ingested e.g. a time in-keeping with biological rhythms and circadian variations, a delivery vehicle of the invention can be beneficially employed in a wide variety of therapeutic and non-therapeutic applications.

A delivery vehicle of the invention may, for example, be used or, used in methods or, used in the manufacture of a composition or medicament, to treat and/or prevent cosmetic issues such as excess weight and aging e.g. by use in methods to modulate hunger and satiety e.g. by delivering a lipid and/or lipophilic active ingredient to a particular location (approximating to a particular pre-determined lag time following ingestion) within the GI tract and thereby activating the ileal break or duodenal break, or, for example, by restricting nutrient/calorie absorption.

Further a delivery vehicle of the invention may be used or, used in methods or, used in the manufacture of a medicament, to treat or prevent sleep disorders, mood disorders or diseased states such as obesity or other conditions affecting the GI tract e.g. ulcerative colitis, Crohn's disease, infections of the GI tract, colorectal cancer and combinations thereof.

Non limiting examples of particular methods wherein a delivery vehicle of the invention may be used are the treatment of ulcerative colitis via repairing the gut lining through the release of phospholipids directly to the colon and, the prevention of colorectal cancer via the release of PUFA and short chain fatty acids e.g. butyrate directly to the colon.

A delivery vehicle of the invention may also be used to avoid or mitigate the metabolic modification or metabolism of a lipid or lipophilic active ingredient (2) comprised therein e.g. by releasing the lipid and/or lipophilic active ingredient (2) after a particular predetermined lag time and thereby minimising or preventing first pass effects. This can reduce the minimum effective concentration of said lipid and/or lipophilic active ingredient (2).

It should be appreciated that all features of the present invention disclosed herein can be freely combined and that variations and modifications may be made without departing from the scope of the invention as defined in the claims. Furthermore, where known equivalents exist to specific features, such equivalents are incorporated as if specifically referred to in this specification.

There now follows a series of non-limiting examples that serve to illustrate the invention.

EXAMPLES

Example 1—Gelatine, β-Lactoglobulin/Xanthan Delivery Vehicle

A delivery vehicle of the invention was manufactured by following a two-step process. The first step involved formation of the core. A pre-emulsion was prepared by dispersing 40 wt % coriander oil in a solution of; 6.67 wt % type B gelatine, 100 mM NaCl, pH 8 at 50-60° C., using a Silverson rotor stator homogeniser (6000 rpm, 2 min). A fine emulsion was then prepared by subjecting the pre-emulsion to high shear/pressure homogenisation using a 2 stage valve homogeniser (Niro Panda 2000, stage 1 1000 bar stage 2 200 bar). The core was then formed by pouring the emulsion into a mould, and then cooling to 4° C. to set the gelling agent to obtain the desired shape.

Figure 1:
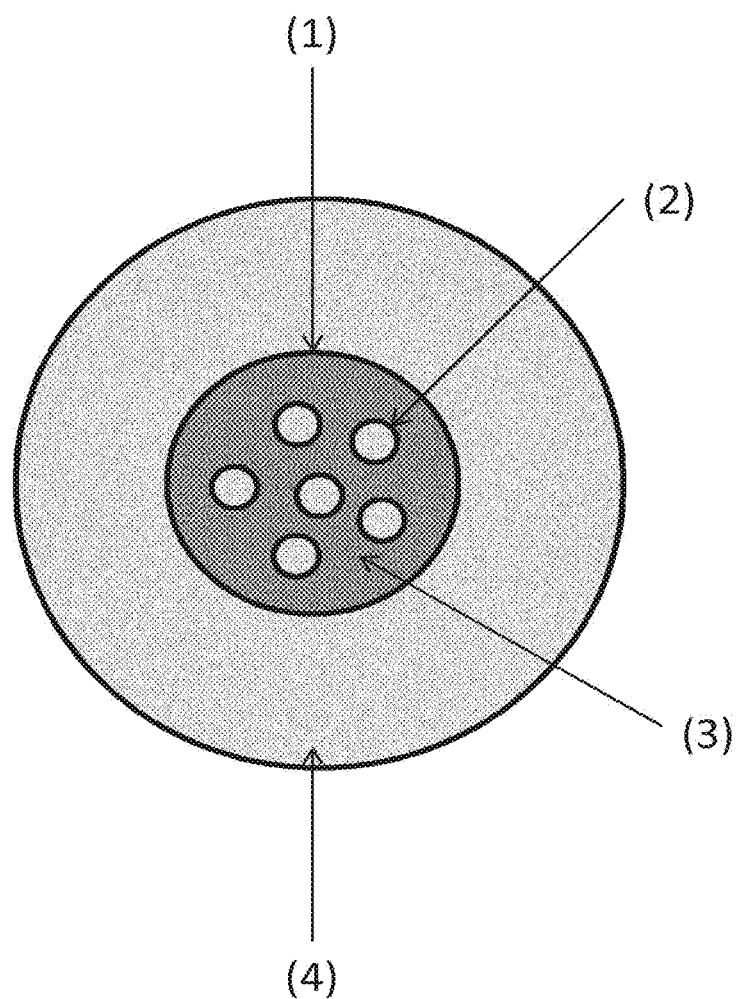
FIG. 1 is an illustrative diagrammatic cross section of a delivery vehicle of the invention.
Figure 2:
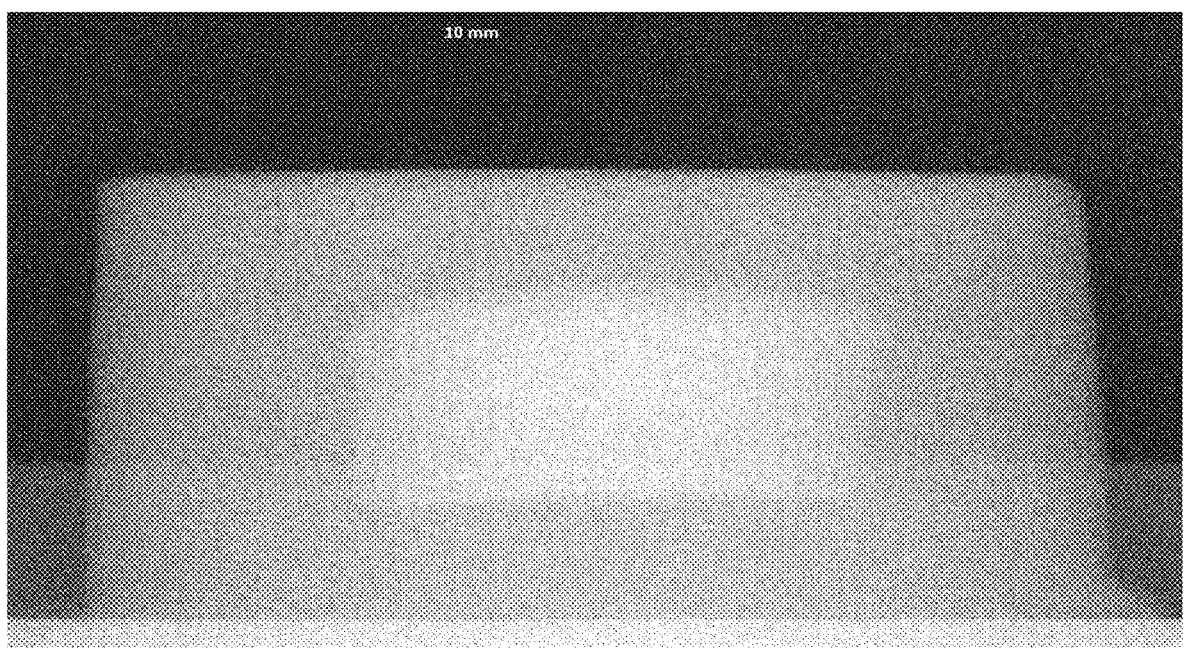
FIG. 2 is a tomographic image of a cross section of a delivery vehicle of the invention.

The core shell structure was then created by placing the core into a mould containing a solution of 8 wt % β-lactoglobulin, 0.9 wt % xanthan 100 mM NaCl, pH 8, (digestible polymer shell solution (hereinafter shell solution)). The core was inserted into the shell solution so that an equal amount of the shell solution surrounded each side of the core. The thickness of the digestible polymer shell was set to 2 mm. The whole system was then heated to 70° C. for 20 minutes to crosslink the shell solution. The resulting core shell structure is depicted in FIG. 1 and was found to give a delay in the release (lag time) of the encapsulated lipid in the small intestine of 190 minutes.

The delay in the release (lag time) of the encapsulated lipid was measured by sequentia I exposure to simulated gastric and intestinal digestion using a pH-STAT protocol according to; Wooster, T. J., Day, L., Xu, M., Golding, M. Oiseth, S. Keogh, J., Clifton, P. Impact of different biopolymer networks on the digestion of gastric structured emulsions. Food Hydrocolloids 2014, 36, 102-114.

The above process was repeated and delivery vehicles having different shell thicknesses were formed. Crosslinking was also carried out at different temperatures. Shell thickness varied from <1 mm to 2.7 mm. The crosslinking temperature varied from 70° C. to 90° C. Table 1 and FIG. 6 gives an overview of the effect that the different shell thicknesses and the different temperatures used for crosslinking have on the lag time before release of the encapsulated lipid (coriander oil).

TABLE 1

Shell thickness and its effect on the lag time before release of the lipid and/or lipophilic active

| Shell Thickness | Release in stomach | Lag time ($T_o$) before the onset of release of lipid (coriander oil) active. | ($T_{1/2}$) Time when at least 50% of the lipid active (coriander oil) is released after the digestible polymer shell is compromised. | ($T_o$) – ($T_{1/2}$) Time between expiry of the lag time and when at least 50% of the lipid active(coriander oil) is released. |
|---|---|---|---|---|
| 1.2 mm | No | 80 min | 110 min | 30 min |
| 2 mm | No | 190 min | 203 min | 13 min |
| 2.2 mm | No | 202 min | 223 min | 21 min |
| 2.6 mm | No | 230 min | 248 min | 18 min |

Example 2—Gelatine, β-Lactoglobulin/Xanthan Delivery Vehicle

A delivery vehicle of the invention was manufactured by following a two-step process. The first step involved formation of the core. A pre-emulsion was prepared by dispersing 40 wt % coriander oil in a solution of; 6.67 wt % type B gelatine, 100 mM NaCl, pH 8 at 50-60° C., using a Silverson rotor stator homogeniser (6000 rpm, 2 min). A fine emulsion was then prepared by subjecting the pre-emulsion to high shear/pressure homogenisation using a 2 stage valve homogeniser (Niro Panda 2000, stage 1 1000 bar stage 2 200 bar). The core was then formed by pouring the emulsion into a mould, and then cooling to 4° C. to set the gelling agent to obtain the desired shape.

The core shell structure was then created by placing the core into a mould containing a solution of 8 wt % β-lactoglobulin, 0.9 wt % xanthan 100 mM NaCl, pH 8, (digestible polymer shell solution (hereinafter shell solution)). The core was inserted into the shell solution so that an equal amount of the shell solution surrounded each side of the core. The thickness of the shell was set to 1.2 mm. The whole system was then heated to 90° C. for 20 minutes to crosslink the shell solution. The resulting core shell structure is shown in FIG. 4 and was found to give a delay in the release of the encapsulated lipid in the small intestine of 315 minutes as compared to 80 minutes for the same composition and thickness heated at 70° C. for 20 minutes.

The delay in digestive release of the encapsulated lipid was measured in the same way as specified in example 1.

Example 3—Gelatine, β-Lactoglobulin/Brominated Vegetable Oil—Low Xanthan Delivery Vehicle A delivery vehicle of the invention was manufactured by following a two-step process. The first step involved formation of the core, which consists of an emulsion trapped within a gel. A pre-emulsion is prepared by dispersing 40 wt % of a triglyceride oil mixture (27% brominated vegetable oil, and 73% high oleic sunflower oil) in a solution of 6.67 wt % type B gelatine, 100 mM NaCl, pH 8 at 50-60° C. using a Silverson rotor stator homogeniser (6000 rpm, 2 min). A fine emulsion is then prepared by subjecting the pre-emulsion to high shear/pressure homogenisation using a 2 stage valve homogeniser (Niro Panda 2000, stage 1 1000 bar stage 2 200 bar). The core is then formed by pouring the emulsion containing gelling agent into a mould, and then cooling to 4° C. to set the gelling agent to obtain the desired shape.

The core shell structure is then created by placing the core into a mould containing a solution of 8 wt % β-lactoglobulin, 0.5 wt % xanthan pH 8 100 mM NaCl. The core is inserted into the shell solution so that an equal amount of shell surrounds each side and the thickness of the shell is 1 mm. The whole system is then heated to 70° C. for 20 minutes to gel the shell. The resulting core shell structure was found to give a delay in the release of the encapsulated lipid in the small intestine of 140 minutes.

The delay in digestive release of the encapsulated lipid was measured in the same way as specified in example 1.

Example 4—Carrageenan, blg/Xanthan Delivery Vehicle

A delivery vehicle of the invention was manufactured by following a two-step process. The first step involves formation of the core, which consists of an emulsion trapped within a gel. A pre-emulsion is prepared by dispersing 60 wt % high DHA/EPA tuna oil in a solution of 2 wt % polysorbate 80 using a Silverson rotor stator homogeniser (6000 rpm, 2 min). A fine emulsion is then prepared by subjecting the pre-emulsion to high shear/pressure homogenisation using a 2 stage valve homogeniser (Niro Panda 2000, stage 1 1000 bar stage 2 200 bar). This emulsion was then diluted with K-carrageenan (Genugel WR-78) and Calcium choride solution to form a final composition of; 40 wt % emulsified fat, 0.6 wt % K-carrageenan and 30 mM CaCl2. The core is then formed by pouring the emulsion containing gelling agent into a mould, and then cooling to 4° C. to set the gelling agent to obtain the desired shape.

The core shell structure was then created by placing the core into a mould containing solution of 8 wt % β-lactoglobulin, 0.9 wt % xanthan pH 8 100 mM NaCl (shell solution). The core was then inserted into the shell solution so that an equal amount of shell surrounded each side and the thickness of the shell was 1 mm. The whole system was then heated to 70° C. for 20 minutes to gel the shell. The resulting core shell structure was found to give a delay in the release of the encapsulated lipid in the small intestine of 50 minutes.

The delay in digestive release of the encapsulated lipid was measured in the same way as specified in example 1.

Example 5—Comparison of the Lipid Release Profile Obtained from i) a 10 wt % Oil in Water Emulsion Stabilised by 0.8 wt % Whey Protein Isolate, ii) a 10 wt % Oil in Water Emulsion Stabilised by 0.8 wt % Whey Protein Isolate Entrapped within a 10 wt % Gelatine Gel A 10 wt % oil-in-water emulsion was prepared by diluting a previously prepared 40 wt % oil-in-water emulsion stabilized by 3.2 wt % whey protein isolate, which was prepared as follows; 240 g of sunflower oil was combined with 360 g of a 5 wt % aqueous protein solution via gentle mixing. A pre-emulsion was prepared by homogenizing the mixture of the aqueous phase with the oil phase using a Silverson L5M-A rotor-stator mixer (Silverson machines, UK) at 7000 rpm for 2 minutes. A fine emulsion was then prepared by further homogenizing the pre-emulsion using a two-stage valve homogenizer (NIRO Soavi Panda, GEA, France), 2 passes at a pressure of 1000 bars for the first stage and 160 bars for the second stage.

A 10 wt % oil-in-water emulsion encapsulated within a 10 wt % gelatin gel was prepared by mixing the above detailed 40 wt % oil-in-water emulsion with a solution containing 13.4 wt % gelatin (Gelita, bovine, type B bloom 240) 100 mM NaCl, pH 8 at 50° C. A gel was then formed by pouring the hot solution into a Teflon mold and cooling at 3-4° C. overnight to create solid gel pieces 4 mm×2 cm×2 cm.

The release profiles of the i) 10 wt % oil in water emulsion stabilised by 0.8 wt % whey protein isolate, and ii) 10 wt % oil in water emulsion stabilised by 0.8 wt % whey protein isolate entrapped within a 10 wt % gelatine gel were then measured in the same way as specified in example 1.

Figure 3:
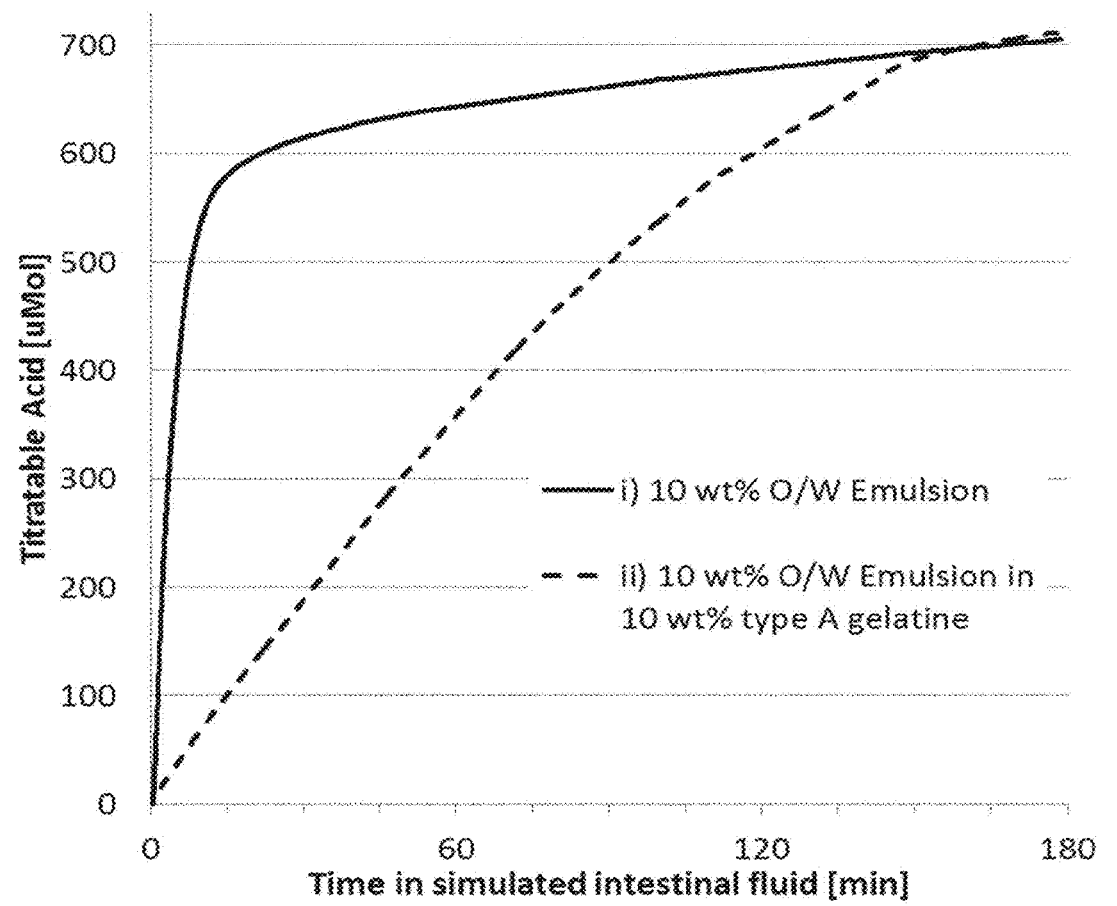
FIG. 3 shows the lipid digestion/release profile in simulated intestinal fluid at 25° C. of i) a 10 wt % oil (sunflower oil) in water emulsion stabilised by 0.8 wt % whey protein isolate, and ii) a 10 wt % oil (sunflower oil) in water emulsion stabilised by 0.8 wt % whey protein isolate entrapped within a 10 wt % gelatine polymeric matrix (gel).

The release profiles of the i) 10 wt % oil in water emulsion stabilised by 0.8 wt % whey protein isolate, and ii) 10 wt % oil in water emulsion stabilised by 0.8 wt % whey protein isolate entrapped within a 10 wt % gelatine gel are shown in FIG. 3.

The invention is claimed as follows:

1. A delivery vehicle comprising a core surrounded by a digestible polymer shell having a melting and/or softening point above the body temperature of an animal or human, wherein the core comprises a lipid and/or lipophilic active ingredient dispersed in a continuous polymer matrix, and wherein the digestible polymer comprised within the digestible polymer shell is a cross linked digestible biopolymer.

2. The delivery vehicle according to claim 1, wherein the polymer matrix is solid below the body temperature of an animal or human and a solid or a liquid at or above the body temperature of an animal or human.

3. The delivery vehicle according to claim 1, wherein the polymer matrix is a biopolymer matrix and wherein the biopolymer is selected from the group consisting of: gelatine, carrageenans, pectin, alginates, agar, gellan, konjac mannan, guar gum, gellan gum, locust bean gum, and combinations thereof.

4. The delivery vehicle according to claim 1, wherein the lipid and/or lipophilic active ingredient is selected from the group consisting of: a pharmaceutical, nutraceutical, supplement, veterinary drug, natural/traditional medicine, food ingredient, and combinations thereof.

5. A delivery vehicle comprising a core surrounded by a digestible polymer shell having a melting and/or softening point above the body temperature of an animal or human,
wherein the core comprises a lipid and/or lipophilic active ingredient dispersed in a continuous polymer matrix,
wherein the digestible polymer comprised within the digestible polymer shell is a cross linked digestible biopolymer, and
wherein the lipid and/or lipophilic active ingredient is selected from the group consisting of: triglycerides, phospholipids, diglycerides, monoglycerides, ceramides, glycolipids and sphingolipids, fish oil, petroselinic acid, eicosapentaenoic acid, carotenoids, phytosterols, phytosterol esters, polyphenols, cholesterol, cholesterol esters, retinol, retinol ester, and combinations thereof.

6. A delivery vehicle comprising a core surrounded by a digestible polymer shell having a melting and/or softening point above the body temperature of an animal or human,
wherein the core comprises a lipid and/or lipophilic active ingredient dispersed in a continuous polymer matrix,
wherein the digestible polymer comprised within the digestible polymer shell is a cross linked digestible biopolymer, and
wherein the core contains an emulsifier.

7. The delivery vehicle according to claim 1, wherein the digestible polymer shell is formed from one or more biopolymer selected from the group consisting of: Bovine serum albumin, β-lactoglobulin, lactoferrin, whey protein isolate patatin, soy protein, canola protein, pea protein, egg protein, lysozyme, pea proteins, lupin, rice protein, gluten, lysozyme, zein, and combinations thereof.

8. A delivery vehicle comprising a core surrounded by a digestible polymer shell having a melting and/or softening point above the body temperature of an animal or human,
wherein the core comprises a lipid and/or lipophilic active ingredient dispersed in a continuous polymer matrix,
wherein the digestible polymer comprised within the digestible polymer shell is a cross linked digestible biopolymer, and
wherein the digestible polymer shell has an average mesh/pore size of <50 nm.

9. A delivery vehicle comprising a core surrounded by a digestible polymer shell having a melting and/or softening point above the body temperature of an animal or human,
wherein the core comprises a lipid and/or lipophilic active ingredient dispersed in a continuous polymer matrix, wherein the digestible polymer comprised within the digestible polymer shell is a cross linked digestible biopolymer, and wherein the core comprises a weighting agent and/or wherein the digestible polymer shell comprises a thickener.

10. A delivery vehicle comprising a core surrounded by a digestible polymer shell having a melting and/or softening point above the body temperature of a subject, wherein the core comprises a lipid and/or lipophilic active ingredient dispersed in a continuous polymer matrix, wherein the digestible polymer comprised within the digestible polymer shell is a cross linked digestible biopolymer, and wherein 50% or more of the lipid and/or lipophilic active ingredient is released within 45 minutes or less and/or 80% or more of the lipid and/or lipophilic active ingredient is release within 75 minutes or less following the expiry of a predetermined lag time following ingestion of said delivery vehicle by the subject.

11. A consumable product comprising a delivery vehicle comprising a core surrounded by a digestible polymer shell having a melting and/or softening point above the body temperature of a subject, wherein the core comprises a lipid and/or lipophilic active ingredient dispersed in a continuous polymer matrix, and wherein the digestible polymer comprised within the digestible polymer shell is a cross linked digestible biopolymer, the composition and/or consumable product is selected from the group consisting of; pharmaceutical products, nutraceutical products, medical foods, veterinary products including pet food and pet care products and, foodstuffs of any kind including functional foods and food supplements.

12. The consumable product according to claim 11, wherein the lipid and/or lipophilic active ingredient is selected from the group consisting of: triglycerides, phospholipids, diglycerides, monoglycerides, ceramides, glycolipids and sphingolipids, fish oil, petroselinic acid, eicosapentaenoic acid, carotenoids, phytosterols, phytosterol esters, polyphenols, cholesterol, cholesterol esters, retinol, retinol ester, and combinations thereof.

13. The consumable product according to claim 11, wherein the core contains an emulsifier.

14. The consumable product according to claim 11, wherein the digestible polymer shell has an average mesh/pore size of <50 nm.

15. The consumable product according to claim 11, wherein the core comprises a weighting agent and/or wherein the digestible polymer shell comprises a thickener.

16. The consumable product according to claim 11, wherein 50% or more of the lipid and/or lipophilic active ingredient is released within 45 minutes or less and/or 80% or more of the lipid and/or lipophilic active ingredient is release within 75 minutes or less following the expiry of a predetermined lag time following ingestion of said delivery vehicle by the subject.

17. The consumable product according to claim 11, wherein the cross linked digestible biopolymer is a thermally cross linked digestible biopolymer.

18. The delivery vehicle according to claim 1, wherein the cross linked digestible biopolymer is a thermally cross linked digestible biopolymer.

19. The delivery vehicle according to claim 5, wherein the cross linked digestible biopolymer is a thermally cross linked digestible biopolymer.

20. The delivery vehicle according to claim 6, wherein the cross linked digestible biopolymer is a thermally cross linked digestible biopolymer.

21. The delivery vehicle according to claim 8, wherein the cross linked digestible biopolymer is a thermally cross linked digestible biopolymer.

22. The delivery vehicle according to claim 9, wherein the cross linked digestible biopolymer is a thermally cross linked digestible biopolymer.

23. The delivery vehicle according to claim 10, wherein the cross linked digestible biopolymer is a thermally cross linked digestible biopolymer.

* * * * *